Figure 2A:
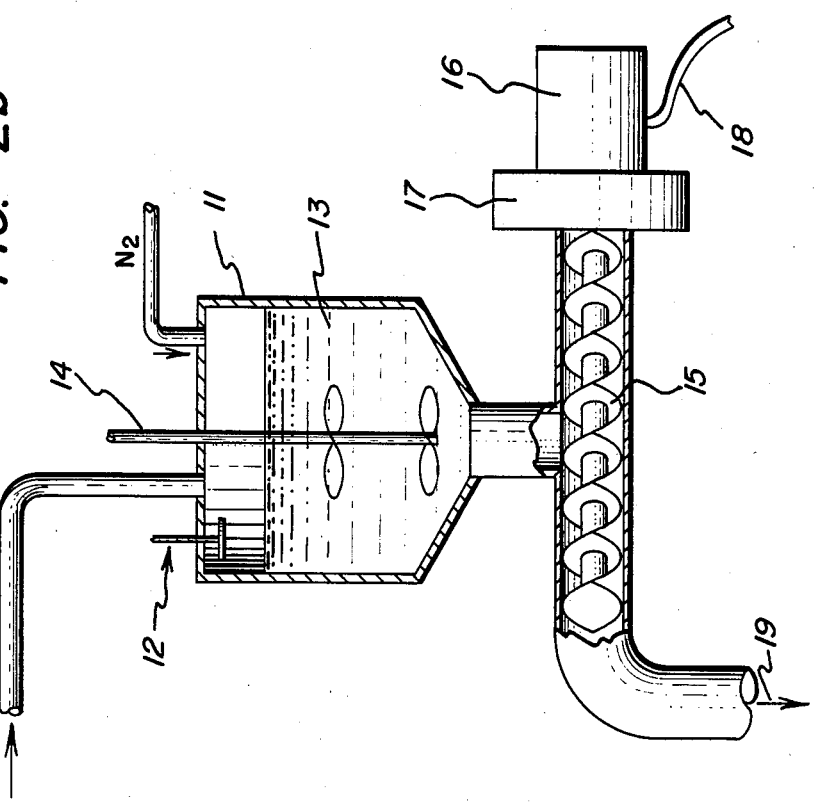

United States Patent [19]

Kosky et al.

[11] Patent Number: 4,810,813

[45] Date of Patent: Mar. 7, 1989

[54] METHOD FOR MAKING REACTION PRODUCTS OF PHOSGENE AND DIHYDRIC PHENOL WITH STABLE SUSPENSION OF DIHYDRIC PHENOL, ALKALI METAL HYDROXIDE AND WATER

[75] Inventors: Philip G. Kosky, Schenectady; James M. Silva, Clifton Park; Thomas J. Fyvie, Schenectady, all of N.Y.

[73] Assignee: General Electric Company, Schenectady, N.Y.

[21] Appl. No.: 77,479

[22] Filed: Jul. 24, 1987

Related U.S. Application Data

[63] Continuation-in-part of Ser. No. 904,580, Sep. 8, 1986, abandoned.

[51] Int. Cl.$^4$ .............................................. C07C 68/00
[52] U.S. Cl. ..................................... 558/281; 528/196; 558/280; 558/282
[58] Field of Search ................... 558/281, 280, 282; 528/196

[56] References Cited

U.S. PATENT DOCUMENTS

| | | | |
|---|---|---|---|
| 3,530,094 | 9/1970 | Schnell et al. | 528/196 |
| 3,787,359 | 1/1974 | Horn et al. | 528/196 |
| 3,959,335 | 5/1976 | Vernaleken et al. | 260/463 |
| 3,966,785 | 6/1976 | Krimm et al. | 558/281 |
| 4,368,315 | 1/1983 | Sikdar | 528/196 |
| 4,515,936 | 5/1985 | Sikdar et al. | 528/196 |
| 4,601,858 | 7/1986 | Shannon et al. | 558/281 |
| 4,638,077 | 1/1987 | Brunelle et al. | 558/281 |

OTHER PUBLICATIONS

U. Becker et al., "The Influence of Physico-Chemical Properties on the Flow Behavior of Concentrated Suspensions", *Ger. Chem. Eng.*, 5 (1982), pp. 12-24.

R. H. Perry et al., *Chemical Engineer's Handbook*, 5th Edition, McGraw-Hill (1973), pp. 6-5 thru 6-14.

*McCannatrol/Diatube Pumps*, Hills-McCanna Company, Form No. 804.

*Wilden Pumps, Air Operated Double Diaphragm*, Wilden Pump & Engrg. Co. (Information at Quaker Pump Co.), Bulletin Advertisement.

*Primary Examiner*—Harold D. Anderson
*Attorney, Agent, or Firm*—William A. Teoli; James C. Davis, Jr.; James Magee, Jr.

[57] ABSTRACT

A method is provided for making reaction products of phosgene and dihydric phenol under interfacial reaction conditions. The dihydric phenol such as BPA is introduced into the reactor in the form of a stable suspension which reduces phosgene hydrolysis, minimizes phosgene escape and effects improved BPA metering into the reactor.

7 Claims, 3 Drawing Sheets

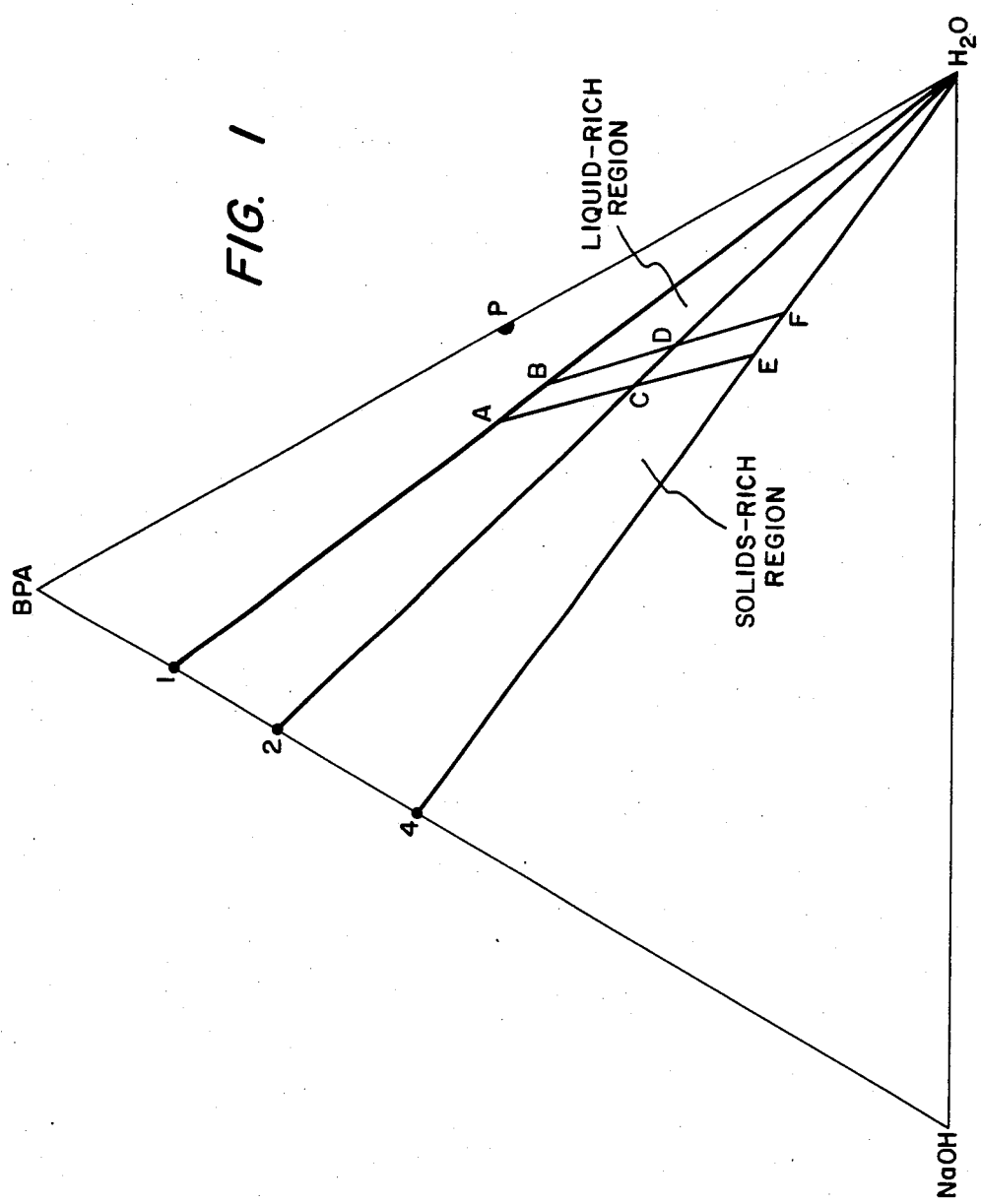

METHOD FOR MAKING REACTION PRODUCTS OF PHOSGENE AND DIHYDRIC PHENOL WITH STABLE SUSPENSION OF DIHYDRIC PHENOL, ALKALI METAL HYDROXIDE AND WATER

CROSS REFERENCES TO RELATED APPLICATIONS

This application is a continuation-in-part of copending application Ser. No. 904,580, filed September 8, 1986 now abandoned, which is assigned to the same assignee as the present invention and incorporated herein by reference.

BACKGROUND OF THE INVENTION

Prior to the present invention, dihydric phenol, such as bisphenol-A (BPA), was phosgenated in a reactor under interfacial reaction conditions resulting in the production of products, such as BPA bischloroformates (BCF), oligomeric carbonate chloroformates, or polycarbonate. There was generally utilized aqueous caustic soda and organic solvent, such as methylene chloride, and the phosgenation reaction was conducted in either a batch or continuous reactor.

Although satisfactory results have been generally achieved during interfacial phosgenation of dihydric phenols, it has been found more difficult to achieve satisfactory results under conditions in which dihydric phenol is fed continuously to the phosgenation reaction as compared to batch-wise conditions. A typical BCF phosgenation reaction mixture can include products having the formulas,

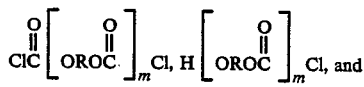 (I)

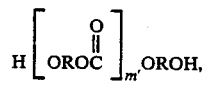

where m can have a value of 1–15, m' is a whole number equal to 0 or an integer having a value of at least 1, and R is a divalent organic radical, such as 2,2-diphenylpropane. A polycarbonate phosgenation mixture can include products having the formula,

 (II)

where R is as previously defined and n can have a value of at least 25.

In determining the stoichiometry between dihydric phenol and phosgene gas in the presence of an aqueous phase, it has been found that wasteful hydrolysis of phosgene can occur. Experience has shown that undue amounts of water can result in excessive phosgene hydrolysis effecting a reduction in the yields of BCF or polycarbonate reaction products per unit of phosgene reacted.

The degree of phosgene hydrolysis also influences the required amount of caustic soda. As a result, there are severe constraints on the amount of each component to be added to the mixture. In particular, BPA is a solid at normal conditions and it is difficult to add it both continuously and consistently, particularly if the rates of addition of other components change. Some of the forms which BPA can be continuously dispensed are:

a. as a dry powder from a hopper using an auger feed screw, b. as an aqueous slurry, c. as a slurry in organic solvent such methylene chloride, and d. as an aqueous solution with NaOH (about 1 mol of BPA per liter of aqueous NaOH having pH ~11).

For batch addition, dry powder can be pre-added to the reactor; however, it is difficult to perform this addition continuously as voids form in the powder which allow phosgene to back-flow into the BPA hopper, thus creating a hazard. Further, the powder flow rate is neither constant, not consistent in this case.

The slurry concept, whether in an aqueous or organic medium, is very difficult to maintain; density differences between BPA (1.18 g/ml), water (1 g/ml), and methylene chloride (1.3 g/ml) allow separation to readily occur so that monitoring of the delivered slurry is a requisite to ensure constant and consistent flow of the BPA phase.

The use of a homogeneous aqueous solution of BPA in NaOH introduces an excessive quantity of water into the reactor so that phosgene hydrolysis is enhanced.

The present invention is based on our discovery that a stable or near-stable suspension, resulting from the agitation of a mixture of BPA and an alkali metal hydroxide in water, as defined hereinafter, can provide a method of continuously adding a dihydric phenol, such as BPA, into a phosgenation process that has the following benefits (i) ease of metering dihydric phenol and maintaining proper dihydric phenol weight proportions with respect to other reaction components, (ii) ease of adjusting dihydric phenol flow rate to changes in phosgene flow rate, (iii) reducing the proportion of water entering the reactor and thereby minimizing the rate of phosgene hydrolysis, and (iv) reducing the hazardous back-flow of phosgene into phosgene-free areas.

As defined hereinafter, the term "stable suspension" means a substantially opaque plural phase material capable of assuming the shape of its container up to a free interface while substantially maintaining its initial appearance without phase separation for a period of at least 30 minutes, under atmospheric conditions, which results from the agitation of a mixture consisting essentially of water, alkali hydroxide and dihydric phenol having a proportion of from about 0.01 to 4 moles of alkali hydroxide, per mole of dihydric phenol, and sufficient water to provide a substantially homogeneous fluid. Preferably, the stable suspension of the present invention comprises by weight (A) 47.9–52.0% bisphenol-A, (B) 52.0–47.9% water, and (C) 0.01–0.2% of alkali metal hydroxide.

The proportion of alkali metal hydroxide should be sufficient to avoid foaming during agitation, and provide a pH of up to about 11. The mixture is stable after an extended shelf period. However, to insure uniformity during use, it is preferred to mildly agitate the suspension.

In instances where the stable suspension can be reacted in 8 hours or less after formulation, the following composition will provide effective results:

(D) about 40–70% water,
(E) about 8 to 16% alkali metal hydroxide, and
(F) about 20–50% BPA, in which higher proportions of water lead to longer periods for which the mixture remains fluid.

STATEMENT OF THE INVENTION

There is provided by the present invention, a method for making phosgene-dihydric phenol reaction product comprising (1) effecting reaction between dihydric phenol and phosgene under interfacial reaction conditions in a reaction vessel in the presence of an alkali metal hydroxide, and (2) recovering phosgene-dihydric phenol reaction product from the mixture (1), where the dihydric phenol is introduced into the reaction vessel in the form of a stable suspension resulting from the agitation of a mixture comprising water, alkali metal hydroxide, and dihydric phenol.

Dihydric phenols which can be used in the practice of the present invention are preferably included by the following formula,

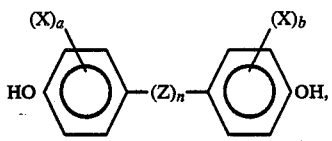

where Z is a divalent radical selected from $-C_yH_{2y}-$

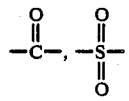

and S, y is an integer equal to 1 to 5 inclusive, n is equal to 0 or 1, X is a member selected from chlorine, bromine, fluorine, a $C_{(1-18)}$ monovalent hydrocarbon radical, such as an alkyl radical, for example methyl, ethyl, propyl or a phenyl radical, or a mixture of such radicals, and a and b are whole numbers equal to 0 to 4 inclusive.

Some of the dihydric phenols which can be utilized in the practice of the present invention are, for example, 2,2-bis(4-hydroxyphenyl)propane (BPA), 2,4'-dihydroxydiphenlymethane, and 4,4'-dihydroxydiphenylmethane. Some of the organic solvents which can be utilized in the practice of the present invention are, for example, methylene chloride, ethylene dichloride, chlorobenzene, dichlorobenzene, chloroform, and like halogenated organic solvents insensitive to the presence of phosgene. There are included among the alkali metal hydroxides, sodium hydroxide, and potassium hydroxide.

The phosgenation reaction can be carried out under standard conditions, such as atmosphere pressure and a temperature of about 14° to 40° C.

In order that those skilled in the art will be better able to understand the practice of the method of the present invention, reference is made to the drawings. There is shown in FIG. 1 a ternary diagram of BPA, NaOH and $H_2O$ having the apexes defined by 100% of the respective components by weight. The preferred stable suspension is a composition, shown at P in FIG. 1 as a semi-circle wholly within the ternary diagram as previously defined.

Figure 2B:
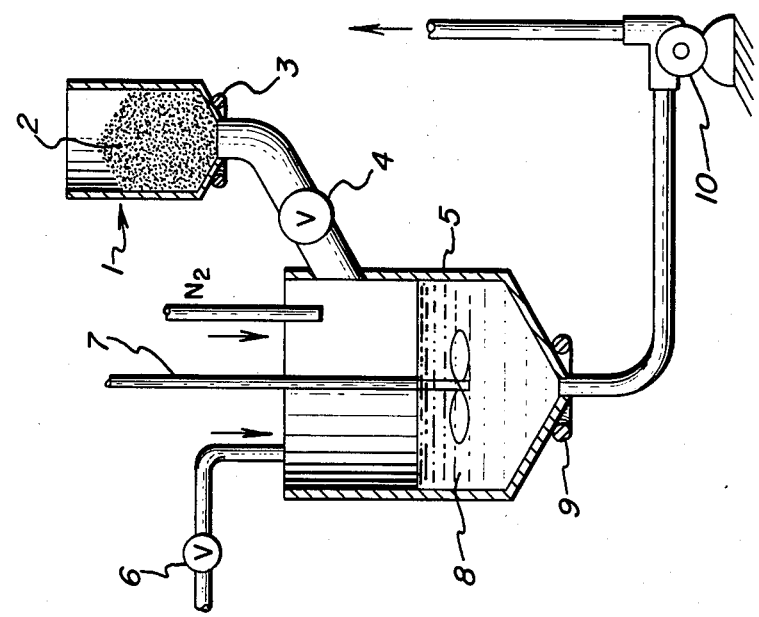
Figure 3:
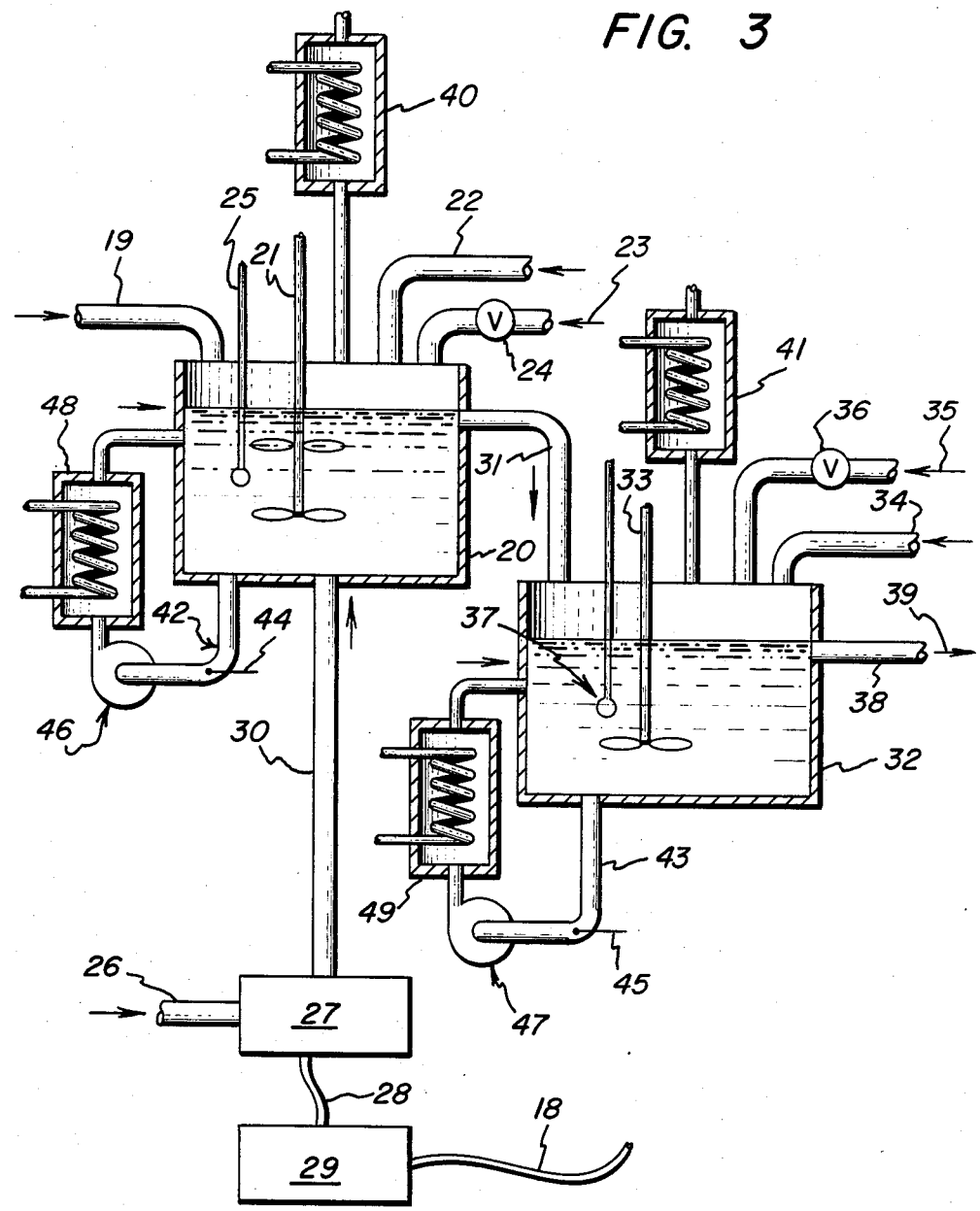

In FIG. 2a, there is shown a hopper containing powdered crystalline BPA, which is fed into a mixing tank with aqueous NaOH. FIG. 2b, there is shown a nitrogen purged feed vessel for receiving the mixture of 2a, which is conveyed by means of an auger to a reaction vessel as shown by FIG. 3.

There is more particularly shown by FIG. 1, a ternary region P having the following coordinates:

|  | BPA | NaOH | $H_2O$ |
| --- | --- | --- | --- |
| P Region (wt %) | 47.9–52.0 | 0.01–0.20 | 47.9–52.0 |

There is also shown by FIG. 1, a ternary diagram having a quadrilateral AB(D)EF(C). The coordinates of these points are as follows (wt %):

| Point | BPA | NaOH | $H_2O$ |
| --- | --- | --- | --- |
| A | 48.5 | 9.0 | 42.5 |
| B | 43.5 | 8.2 | 48.5 |
| C | 30.0 | 11.1 | 59.0 |
| D | 34.5 | 12.7 | 52.6 |
| E | 19.4 | 13.5 | 67.0 |
| F | 22.6 | 16.0 | 61.5 |

Points 1, 2 and 4 along the NaOH-BPA axis, are the NaOH/BPA mole ratios. Limits on water addition are shown by "Liquid-Rich Region", with excess water and "Solids-Rich Region" with excess solid. If an attempt is made to feed a slurry to the auger screw that is too "liquid-like", it separates and exhibits the unsatisfactory rheology of a plain water/BPA slurry. If an attempt is made to feed a too solid-like slurry with an auger screw, it can cake, and voids form in the auger screw, causing the feed rate to be inconsistent and decoupling the quantity fed from the rate of turning of the auger. Furthermore, a continuous void through the caked slurry will provide a path for phosgene back-leakage.

More particularly, FIG. 2a shows a hopper tank at 1, holding BPA solid feed at 2 which is metered by a conventional weight transducer at 3, and a shut-off valve at 4, into a mixing tank at 5. The mixing tank is purged with nitrogen and there is fed into the mixing tank, a predetermined amount of sodium hydroxide solution of requisite strength through the valve at 6. A stirrer is shown at 7. After the BPA is stirred for a period of about 20 minutes or more, depending upon the size of the crystals, a stable suspension is formed at 8. A conventional weight transducer is shown at 9 as an alternative to transducer 3 for the metering of BPA from tank 1 to tank 5. The stable BPA suspension can be pumped via a slurry pump at 10 into a feed vessel 11 shown in FIG. 2b, which also is purged with nitrogen. A level sensor at 12 limits the amount of the stable suspension in vessel 11 which is continuously agitated slowly with stirrer 14. The stable suspension at 13, is metered into the process via duct 19 by an auger at 15 which is powered by a motor generator set at 16 through a gear reduction box at 17. The clearance between the auger screw and its concentric duct should be sufficiently small to minimize any aqueous solution flow resulting in a change in slurry composition. The motor generator set is controlled by a signal at 18 from a phosgene flow meter shown at 27 in FIG. 3.

There is shown more particularly in FIG. 3, a phosgenation vessel at 20 having a stirrer at 21 to which there is fed methylene chloride at 22, additional sodium hydroxide solution at 23 via valve 24 controlled via pH probe 25. Stable BPA suspension generated in the apparatus of FIG. 2, is fed into the reactor through duct 19 and phosgene is fed into the bottom of the reactor at 30. Phosgene enters the process at 26 and is metered through flow meter 27 which produces an electrical signal; the electrical signal transmitted by line 28 is processed by an amplifier 29 which produces the control signal 18 proportional to the phosgene flow for its Motor Generator set 16 of FIG. 2b. Reaction product is fed at 31 which can be equipped with filters to retain BPA, if necessary, into a vessel for a cyclization reaction at 32 having a stirrer at 33 and a pH probe at 37 to maintain a pH at about 11-13. The resulting cyclic polycarbonate is conveyed through line 38 to purification steps at 39. Additional solvent may be admitted through duct 34 and aqueous NaOH solution 35 through valve 36 controlled via pH probe 37.

The heats of reaction generated within vessels 20 and 32 are removed by condensing solvent in condensers 40 and 41. However, optionally, additional heat exchange loops 42 and 43 using temperature sensors 44 and 45 may also be used. Pumps 46 and 47 are operated as needed and cool the reaction mixtures in heat exchangers 48 and 49.

Those skilled in the art know that a different BPA to phosgene ratio, utilizing a BPA in the form of a stable suspension as previously described would provide polycarbonate if fed to a continuous polycarbonate reactor.

In order that those skilled in the art will be better able to practice the present invention, the following example is given by way of illustration and not by way of limitation. All parts are by weight.

EXAMPLE 1

A 1 liter glass tank reactor was fitted with 4 glass baffles, an agitator, a vented condenser, a pH electrode, a thermometer, a dip tube for phosgene addition, a tube for addition of 50 wt. % NaOH aqueous solution for pH control, and an auger feed system for the addition of an aqueous NaOH suspension of BPA. The BPA suspension comprised a mixture of 228 parts BPA, 60 parts NaOH, and 374 parts $H_2O$.

The reactor was initially charged with 500 ml $CH_2Cl_2$, 100 ml $H_2O$, and 10 gm solid BPA. The agitation was begun, and both phosgene gas was sparged into the reactor at 3.63 gm/min and the suspension was fed into the reactor at an average rate of 15.3 gm/min. The BPA suspension was fed for 26 minutes, and the $COCl_2$ was fed for 38.5 minutes. The reaction was started at room temperature and reached refluxing conditions after about 5 minutes of phosgenation. The reaction pH was controlled to the range 2-5 by the addition of an aqueous solution of 50 wt. % NaOH. After the phosgene was shut off, the reactor was purged with nitrogen for 2 minutes and a sample was taken and analyzed by Liquid Chromatography to yield the results shown in Table I.

The above procedure was repeated except an addition funnel was used to feed a solution of BPA in aqueous NaOH.

The reactor was initially charged with 400 ml $CH_2Cl_2$, 100 ml $H_2O$, and 10 gm solid BPA. A solution of BPA in aqueous NaOH was prepared by adding 104 gm BPA and 42 ml 50 wt. % NaOH to enough $H_2O$ to yield 500 ml solution. This solution was loaded into an addition funnel. The agitation was begun and $COCl_2$ was sparged into the reactor at 3.63 gm/min for 30 minutes. The BPA/NaOH solution was added at an average of 17.9 cc/min for 28 minutes. The reaction pH was controlled in the range of 2-5 by the addition of an aqueous solution of 50 wt. % NaOH. At the end of the phosgenation time, the reactor was purged with nitrogen for 2 minutes and the organic phase was sampled and analyzed by Liquid Chromatography to yield the results shown in Table I, where "MCF" is monochloroformate, "BCF" is bischloroformate and L-2, and L-3 are OH terminated linear dimer and trimer:

TABLE I

| | mol BPA group*/liter organic product | |
|---|---|---|
| Component | Suspension | Solution |
| BPA | 0.000 | 0.077 |
| $COCl_2$** | 0.176 | 0.122 |
| BPA-MCF | 0.027 | 0.215 |
| BPA-BCF | 0.247 | 0.117 |
| Dimer-MCF | 0.028 | 0.168 |
| Dimer-BCF | 0.232 | 0.082 |
| 3-BCF | 0.177 | 0.118 |
| 4-BCF | 0.130 | 0.064 |
| 5-BCF | 0.071 | 0.012 |
| 6-BCF | 0.048 | 0.000 |
| 7-BCF | 0.027 | 0.000 |
| L-2 + L-3 | 0.003 | 0.117 |
| Total BPA units | | |
| liter organic | 0.99 | 0.97 |
| % MCF | 5.5 | 39.5 |
| % (L-2 + L-3) | 0.25 | 12 |
| % $COCl_2$ Hydrolysis | 24 | 42 |
| % $COCl_2$ Escape Through BPA Feed System | ∞0 | ∞0 |

*mols BPA groups in a given species per liter organic phase
**for $COCl_2$, the number in the table is mole $COCl_2$/liter organic phase In Table I the following definitions are used:

$$\% \text{ MCF} = 100 * \frac{\text{mols BPA groups BPA-MCF and Dimer-MCF}}{\text{total mols BPA groups in product}}$$

$$\% \text{ (L-2 + L-3)} = 100 * \frac{\text{mols BPA groups as L-2 and L-3}}{\text{total mols BPA groups in product}}$$

$$\frac{\% \text{ COCl}_2 \text{ Hydrolysis}}{100} = 1 - \frac{\text{mols (COCl}_2 + \text{organic carbonate} + \text{chloroformate) product}}{\text{mols COCl}_2 \text{ fed}}$$

The above results show that the % of phosgene hydrolysis was considerably higher in the solution run as compared to the suspension. In addition, no phosgene escaped through the continuous BPA feed system in either run. The nature of the reaction products such as partially phosgenated BPA, i.e. BPA-MCF, Dimer-MCF, and L-2 and L-3 are shown to be much higher in the solution run versus the suspension run.

EXAMPLE 2

A stable suspension of equal parts by weight of BPA and water and a small amount of 19N NaOH solution to bring the pH of the stable lsuspension to about 10.5 was continuously phosgenated in a reactor. BPA and water were fed into the reactor at a rate of 10.26 grams/minute equivalent to a volumetric flow of 10.0 ml/minute, while phosgene was continuously fed into the reactor at 5 grams/minute and methylene chloride was continuously fed at a rate of 23 ml/minute. The reaction was conducted continuously over a 6-hour period and the fluidity of the stable suspension of the BPA and water did not appear to change. The reactor ws held at a pH nominally between 3 and 6 by continuously adding approximately 11.5 ml/minute of 6N NaOH solution. After the initial transients were allowed to stabilize and the mixture had been refluxing for more than an hour, samples of the organic phase of the product were taken, quenched at 0° C. in excess phenol, triethylamine and methylene chloride and subjected to LC analysis. The results, after 6 hours of continuous operation, were found to be substantially equivalent to those obtained from the stable suspension in Table I.

Although the above examples are directed to only a few of the very many variables which can be utilized in the practice of the method of the present invention, it should be understood that the method of the present invention employs a much larger variety of dihydric phenols, alkali metal hydroxides, organic solvents, and the like as well as procedures for making polycarbonate as shown in the description proceeding such example.

What is claimed and sought to be protected by Letters Patent of the United States is as follows:

1. A continuous method for making phosgene-dihydric phenol reaction products whereby phosgene hydrolysis and back-flow are reduced comprising (1) effecting reaction between dihydric phenol and phosgene under interfacial reaction conditions in a reaction vessel in the presence of alkali metal hydroxide, and
    (2) recovering phosgene-dihydric phenol organic reaction products, wherein the dihydric phenol is metered into the reaction vessel as a stable suspension resulting from the agitation of a mixture comprising water, alkali metal hydroxide, and dihydric phenol comprising by weight:

(A) 47.9–52.0% bisphenol-A,
    (B) 52.0–47.9% water, and
    (C) 0.01–0.2% alkali metal hydroxide.

2. The method of claim 1, wherein the dihydric phenol is bisphenol-A.

3. The method of claim 1, wherein the phosgene-dihydric phenol reaction product is a bischloroformate or mixture of oligomeric carbonate mono- and bis-chloroformates.

4. The method of claim 1, wherein the alkali metal hydroxide is sodium hydroxide.

5. The method of claim 1, wherein sufficient methylene chloride is utilized in the reaction between bishpenol-A and phosgene to achieve interfacial reaction conditions.

6. The method of claim 1, wherein bisphenol-A is introduced into the reaction vessel by using an extruder.

7. The method of claim 1, wherein bishpenol-A is introduced in the reactor vessel by an auger screw.

* * * * *